US00PP37552P2

(12) United States Plant Patent
Moucheboeuf

(10) Patent No.: US PP37,552 P2
(45) Date of Patent: Aug. 4, 2026

(54) ***DIANTHUS* PLANT NAMED 'KLEDA28883'**

(50) Latin Name: ***Dianthus* x *allwoodii* hort.**
Varietal Denomination: KLEDA28883

(71) Applicant: KLEMM + SOHN GMBH & CO. KG, Stuttgart (DE)

(72) Inventor: Laetitia Moucheboeuf, Exeter (GB)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/370,989

(22) Filed: Oct. 28, 2025

(51) Int. Cl.
*A01H 5/02* (2018.01)
*A01H 6/30* (2018.01)

(52) U.S. Cl.
USPC ..... Plt./278

(58) Field of Classification Search
USPC ..... Plt./273, 278
See application file for complete search history.

(56) References Cited

U.S. PATENT DOCUMENTS

PP32,445 P2 * 11/2020 Moucheboeuf ..... A01H 6/305
Plt./278

* cited by examiner

*Primary Examiner* — Susan McCormick Ewoldt
(74) *Attorney, Agent, or Firm* — Weatherly IP Solutions, LLC; John E. Pritchard; James M. Weatherly

(57) ABSTRACT

A new *Dianthus* plant designated 'KLEDA28883' particularly distinguished coral colored flowers that transition from dark coral to light coral with age of the flowers; and a compact mounding habit, is disclosed.

1 Drawing Sheet

Genus and species: *Dianthus* x *allwoodii* hort.
Variety denomination: 'KLEDA28883'.

BACKGROUND OF THE NEW PLANT

The present invention comprises a new and distinct variety of *Dianthus*, botanically known as *Dianthus* x *allwoodii* hort. and hereinafter referred to by the variety name 'KLEDA28883'. 'KLEDA28883' originated from cross pollination of the proprietary female parent '14.025' (unpatented) and the male parent 'PIE.095' (unpatented) between May and August 2018 in Ashcombe, Dawlish, United Kingdom. Seed obtained from the cross were sown, grown, and during July 2019, a progeny plant was selected and named 'KLEDA28883'.

In September 2019, 'KLEDA28883' was first vegetatively propagated by vegetative cuttings in Ashcombe, Dawlish, United Kingdom and was found to reproduce true to type in successive generations of asexual propagation.

SUMMARY

The following are the most outstanding and distinguishing characteristics of 'KLEDA28883' when grown under normal horticultural practices in Ashcombe, Dawlish, United Kingdom.

1. Coral colored flowers that transition from dark coral to light coral with age of the flowers; and
2. A compact mounding habit.

DESCRIPTION OF THE PHOTOGRAPHS

This new *Dianthus* plant is illustrated by the accompanying photographs taken during June 2024 of a 9-month-old whole plant of 'KLEDA28883' that was grown indoors at Dawlish, Devon, United Kingdom. The photographs show the foliage, buds, and flowers and the colors shown are as true as can be reasonably obtained by conventional photographic procedures.

DESCRIPTION

The following detailed descriptions set forth the distinctive characteristics of 'KLEDA28883'. The data which define these characteristics were collected in June 2025 from a 9-month-old asexual reproduction grown in a glass house over the winter in low-temperature conditions at Dawlish, Devon, United Kingdom. Color references are to The R.H.S. Colour Chart of The Royal Horticultural Society of London (R.H.S.), 6$^{th}$ edition (2015).

Classification:
- *Family*.—Caryophyllaceae.
- *Botanical*.—*Dianthus* x *allwoodii* hort.
- *Designation*.—'KLEDA28883'.
- *Type*.—Perennial carnation.

Parentage:
- *Female parent*.—'14.025' (unpatented).
- *Male parent*.—'PIE.095' (unpatented).

Plant:
- *Propagation type*.—Vegetative shoot cuttings.
- *Time to produce a rooted young plant*.—5 weeks to produce a rooted plug.
- *Root description*.—Fibrous, fine, color R.H.S. 156D.
- *Rooting habit shape*.—Fibrous.
- *Plant form*.—Compact mounding habit, upright.
- *Plant height*.—38.0 cm to 42.0 cm.
- *Plant diameter or spread*.—21.0 cm to 23.0 cm.

Lateral branches/stems (shoot before elongation):
- *Shape of the branch in cross-section*.—Circular.
- *Hollowness of the branch*.—Absent.

*Length.*—13.0 cm to 15.0 cm.
*Diameter.*—0.4 cm.
*Internode length.*—0.3 cm to 0.5 cm.
*Internode quantity per branch.*—6 to 7.
*Number of internodes per branch/stem.*—6 to 7.
*Node length.*—0.2 cm to 0.3 cm.
*Node diameter.*—0.3 cm.
*Texture.*—Smooth.
*Color* (*in sheathing zone*).—Between R.H.S. 145B and R.H.S. 145D.

Lateral branches/stems (flower stem):
*Shape of the branch in cross-section.*—Circular.
*Hollowness of the branch.*—Absent.
*Length.*—34.0 cm to 36.0 cm.
*Diameter.*—0.3 cm.
*Internode length.*—1.0 cm to 8.0 cm.
*Internode quantity per branch/stem.*—5 to 6 up to breaking point of the flower stem.
*Node length.*—0.4 cm to 0.5 cm.
*Node diameter.*—0.5 cm to 0.6 cm.
*Texture.*—Smooth.
*Color.*—R.H.S. N189C.
*Flower clustering on the lateral branch.*—None.

Foliage:
*Arrangement.*—Opposite, sheathing and spiraling up the stem.
*Length.*—11.0 cm to 15.0 cm.
*Width.*—0.3 cm.
*Shape.*—Linear.
*Apex.*—Acute.
*Base.*—Decurrent.
*Margin.*—Entire.
*Texture* (*both upper and lower surfaces*).—Smooth.
*Cross-section of the leaf.*—Flat or vary weakly concave.
*Curvature of the leaf.*—Absent or very weakly recurved.
*Glaucosity of the leaf.*—Medium to strong.
*Leaf color* (*both immature and mature*).—Immature: Upper surface: R.H.S. 189B. Lower surface: R.H.S. 189B. Mature: Upper surface: R.H.S. 189A. Lower surface: R.H.S. 189A.
*Venation pattern.*—Absent.

Flowers:
*Flower type and habit.*—Single and round.
*Fragrance.*—Present.
*Position of the flowers compared to the foliage of the plant.*—Far above.
*Profile of both the upper and lower part in the lateral view.*—Flat.
*Diameter of the flower.*—5.0 cm to 5.5 cm.
*Natural flowering season.*—Spring to autumn.
*Number of flowers per spray.*—5 to 7.
*Flower longevity on the plant.*—10 to 20 days.

Buds (before cracking color):
*Length.*—3.0 cm.
*Diameter.*—1.0 cm.
*Shape.*—Oblong.
*Color.*—Upper part R.H.S. 138A; lower part R.H.S. 144B.
*Extrusion of the styles at the bud stage.*—Absent.

Corolla:
*Quantity of petals and arrangement.*—5 petals, persistent, apopetalous and overlapping.
*Corolla height.*—1.0 cm to 1.5 cm.
*Petal length.*—5.0 cm to 5.5 cm.
*Petal width.*—3.6 cm to 3.9 cm.
*Petal shape.*—Fan shaped.
*Petal apex.*—Obtuse.
*Petal base.*—Acute.
*Petal margin.*—Crenate-dentate.
*Depth of petal margin.*—Shallow.
*Petal texture* (*both upper and lower surfaces*).—Smooth.
*Petal color.*—Immature: Upper surface: Closest to R.H.S. 50A. Lower surface: Closest to R.H.S. 50A. Mature: Upper surface: Closest to R.H.S. 52A and R.H.S. 52B. Lower surface: Closest R.H.S. 52B.
*Macule.*—Not present.

Calyx:
*Quantity of sepals and arrangement.*—Composed of 5 sepals, fused up to 0.7 cm below the apex.
*Longitudinal axis of the lobes of the calyx.*—Straight.
*Shape.*—Cylindrical.
*Calyx height.*—3.0 cm to 3.3 cm.
*Calyx diameter* (*at the apex*).—1.1 cm to 1.3 cm.
*Sepal texture* (*both upper and lower surfaces*).—Smooth.
*Sepal color.*—Upper surface: R.H.S. N138B at the apex and R.H.S. 144D at the base. Lower surface: R.H.S. 144D.
*Position of the outer lobes of the epicalyx in relation to the calyx.*—Adpressed and free.
*Apex shape of the outer lobes of the epicalyx.*—Acuminate.
*Tip length of the outer lobes of the epicalyx.*—Short.
*Position of the inner lobes of the epicalyx in relation to the calyx.*—Adpressed.
*Apex shape of the inner lobes of the epicalyx.*—Medium acuminate.
*Tip length of the inner lobes of the epicalyx.*—Short.

Peduncles:
*Length.*—34.0 cm to 36.0 cm.
*Diameter.*—0.2 cm.
*Strength.*—Strong.
*Texture.*—Smooth.
*Color.*—R.H.S. 189B.

Reproductive organs:
*Stamens.*—Quantity per flower: 10. Filament length: 3.0 cm to 3.3 cm. Filament color: R.H.S. NN155C. Anther length: 0.3 cm. Anther diameter: 0.1 cm. Anther color: 76B (before dehiscence). Anther attachment and shape: Dorsifixed, linear. Pollen amount: High.
*Pistils.*—Quantity per flower: 1, each with 2 styles. Length: 3.5 cm to 4.0 cm. Stigma: Color: R.H.S. NN155B. Shape: Linear and hairy along the style. Length: 2.8 cm to 3.0 cm. Diameter: 0.1 cm. Style: Color: R.H.S. 76D. Length: 0.5 cm to 1.0 cm, along the stigma. Diameter: 0.1 cm. Ovary: Size: 0.8 cm in length and 0.6 cm to 0.8 cm in diameter. Shape: Rhombic. Color: R.H.S. 145A on the apical half and R.H.S. 145C on the basal half.

Seeds: None observed.

Disease and insect resistance: No particular disease or insect resistance observed.

COMPARISON OF 'KLEDA28883' WITH PARENTAL LINE AND KNOWN VARIETY

'KLEDA28883' is distinguished from the parent as described in Table 1.

TABLE 1

| Comparison with Parental Line | | | |
|---|---|---|---|
| Characteristic | 'KLEDA28883' | Female parent | Male Parent |
| Number of flower stems | More flowers than the female parent; about the same as the male parent | Fewer flowers than 'KLEDA28883' | Same as 'KLEDA28883' |
| Plant Height | Taller than the female parent, about the same height as the male parent | Shorter than 'KLEDA28883' | Same as 'KLEDA28883' |
| Flower petal edge and arrangement | Crenate-dentate and rounded where the dentation is less shallow than the female parent and about as shallow as the male parent. | Crenate-dentate very shallow and imperfect arrangement | Crenate-dentate medium and round |
| Flower Color | Medium coral color that is the same as the female parent but is darker than the male parent | Medium coral | Light coral |

TABLE 1-continued

'KLEDA28883' can be compared to the commercial *Dianthus* variety 'WP19 Pie65' (U.S. Plant Pat. No. 32,445). Differences between the varieties are described in Table 2.

TABLE 2

| Comparison with Similar Variety | | |
|---|---|---|
| Characteristic | 'KLEDA28883' | 'WP19 Pie65' |
| Flower color | Medium coral | Dark red |

I claim:

1. A new and distinct variety of *Dianthus* plant designated 'KLEDA28883' as illustrated and described herein.

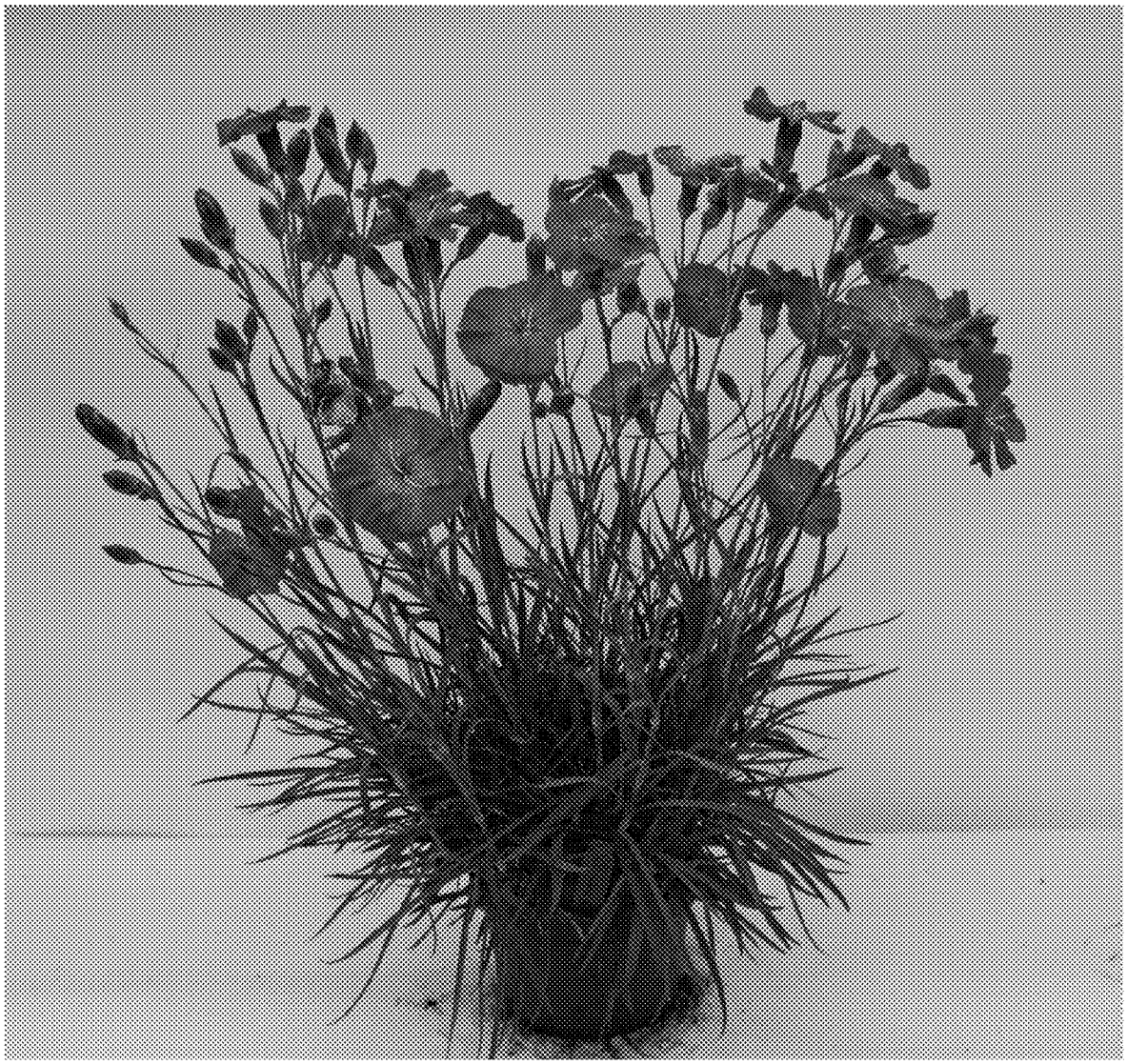

* * * * *